United States Patent [19]

Leach et al.

[11] 4,071,566
[45] Jan. 31, 1978

[54] PREPARATION OF CRESOLS AND XYLENOLS FROM TETRAMETHYLPHENOLS AND PENTAMETHYLPHENOL

[75] Inventors: Bruce E. Leach; Charles M. Starks, both of Ponca City, Okla.

[73] Assignee: Continental Oil Company, Ponca City, Okla.

[21] Appl. No.: 651,667

[22] Filed: Jan. 22, 1976

[51] Int. Cl.² .............................................. C07C 39/04
[52] U.S. Cl. .................... 260/621 D; 260/621 R; 260/624 R
[58] Field of Search ........... 260/621 D, 624 E, 624 C, 260/624 R, 621 E, 621 R

[56] References Cited

U.S. PATENT DOCUMENTS

| | | | |
|---|---|---|---|
| 2,448,942 | 9/1948 | Winlkler et al. | 260/621 R |
| 3,446,856 | 5/1969 | Hamilton | 260/621 R |
| 3,998,892 | 12/1976 | Leach | 260/621 E |

FOREIGN PATENT DOCUMENTS

| | | | |
|---|---|---|---|
| 1,014,550 | 7/1957 | Germany | 260/624 E |
| 1,001,998 | 2/1957 | Germany | 260/621 D |
| 1,291,191 | 10/1972 | United Kingdom | 260/621 D |

OTHER PUBLICATIONS

Jelinck "Chem. Abstract", vol. 55, p. 7357 (1961).
Wells et al., "J. Applied Chem.", vol. 2, p. 159 (1962).

Primary Examiner—James O. Thomas, Jr.
Assistant Examiner—W. B. Lone
Attorney, Agent, or Firm—Bayless E. Rutherford, Jr.

[57] ABSTRACT

Cresols and xylenols are prepared by reacting a mixture of tetramethylphenols and pentamethylphenol with phenol in the liquid phase in the presence of a catalyst selected from the group consisting of activated carbon, magnesium oxide, magnesium carbonate and magnesium hydroxide.

10 Claims, No Drawings

PREPARATION OF CRESOLS AND XYLENOLS FROM TETRAMETHYLPHENOLS AND PENTAMETHYLPHENOL

CROSS-REFERENCE TO RELATED APPLICATIONS

Application Ser. No. 632,335, filed Nov. 17, 1975, wherein the inventor Bruce E. Leach, and having the same assignee as the present application, is directed to a process for preparing prehnitenol (2,3,4,5-tetramethylphenol). The process comprises reacting pentamethylphenol with phenol in the liquid phase using a catalyst selected from the group consisting of activated carbon, magnesium oxide and calcium oxide.

Application Ser. No. 651,659, filed the same date as the present application, and having the same inventors and assignee as the present application, is directed to a process for preparing cresols and xylenols from a mixture of tetramethylphenols and pentamethylphenol. The process comprises reacting the mixture of tetramethylphenols and pentamethylphenol with phenol in the liquid phase in the presence of a catalyst which can be synthetic silica alumina, activated alumina or a combination of activated alumina and metaboric acid.

FIELD OF THE INVENTION

The invention is in the general field of preparation of cresols and xylenols, and particularly in the field of preparing these materials from a mixture of tetramethylphenols and pentamethylphenol.

BACKGROUND

The methylation of phenol using alumina catalyst produces a bottoms product which currently has no known use except as a fuel for oil-burning furnaces. The bottoms product is a complex mixture of highly alkylated phenols and contains significant amounts of tetramethylphenols and pentamethylphenol.

Cresols are known to be useful as a disinfectant. Moreover, xylenols are known to be useful as a wire enamel solvent. In view of this, it is thus apparent that conversion of the tetramethylphenols and pentamethylphenol, in the bottoms product, to cresols and xylenols would increase significantly the value of the bottoms product. Our invention, therefore, provides a means of increasing the value of the bottoms product.

PRIOR ART

A search of the prior art on a related invention produced numerous patents directed to the disproportionation or transmethylation of polyalkylphenols.

However, an IFI computer search did not produce any references teaching disproportionation of polymethylated phenols in the liquid phase in the presence of phenol and activated carbon or magnesium oxide as the catalyst.

BRIEF SUMMARY OF THE INVENTION

Briefly stated, the present invention is directed to a process for preparing cresols and xylenols by reacting a mixture of tetramethylphenols and pentamethylphenol with phenol in the liquid phase in the presence of a catalyst selected from the group consisting of activated carbon, magnesium oxide, magnesium carbonate and magnesium hydroxide.

More specifically, the present invention is directed to a process for preparing cresols and xylenols by reacting an admixture of polymethylated phenols, containing substantial amounts of tetramethylphenols and pentamethylphenol, with phenol in the liquid phase in the presence of a catalyst selected from the group consisting of activated carbon, magnesium oxide, magnesium carbonate and magnesium hydroxide.

The preferred catalysts are activated carbon and magnesium oxide.

DETAILED DESCRIPTION

While mixtures of pure tetramethylphenols and pentamethylphenol can be used, usually because of availability there will be used materials such as the bottoms product from methylation of phenols. These materials are complex mixtures of methyl-substituted phenols. In order to be suitable for my process the bottoms product (or reaction feedstock) must contain substantial quantities of both tetramethylphenols and pentamethylphenol. More specifically, the bottoms product should contain at least about 10 weight percent, preferably at least about 20 weight percent tetramethylphenols and at least about 10 weight percent, preferably at least about 20 weight percent pentamethylphenol. The bottoms product is characterized further in that usually it contains no more than 10 weight percent dimethylphenols. More usually, it contains no more than 4 weight percent dimethylphenols.

Any commercial grade phenol is suitable in the process.

Any ratio of phenol to the mixture of tetramethylphenols and pentamethylphenol can be used. However, in order to obtain better yields it is desirable to use at least a stoichiometric amount of phenol. Amounts above stoichiometric (e.g. 2:1) are more suitable since still better results are obtained. Generally, it is not desirable to use above a 3:1 stoichiometric amount since the results do not justify the increased cost.

Suitable catalysts for use in our process include activated carbon, magnesium oxide, magnesium carbonate and magnesium hydroxide. The preferred catalysts are activated carbon and magnesium oxide. Inasmuch as all of the foregoing materials are well-known to those skilled in the art further description is not believed necessary.

A suitable amount of catalyst is in the range of about 0.1 to about 5 weight percent based on the total amount of phenol, tetramethylphenols and pentamethylphenol. On the same basis the preferred amount of catalyst is in the range of about 0.5 to about 2 weight percent.

PROCESS CONDITIONS

A suitable temperature for conducting the process is in the range of about 375° to about 500° C. Preferably, the temperature is in the range of about 400° to about 450° C.

The process is conducted under sufficient pressure to maintain the reactants in a liquid phase. Usually, a pressure in the range of about 30 to about 125 atmospheres is suitable.

The process can be conducted on a batch or continuous basis.

Knowing the conditions stated hereinbefore any person skilled in the art can readily determine the optimum reaction time.

Usually, in a continuous process, the residence time is at least 5 minutes.

Also, usually, in a batch process, the reaction time is in the range of about 30 minutes to about 3 hours.

On completion of the reaction the product mixture is allowed to come to ambient conditions. If desired, the cresols and xylenols can be separated from the product mixture by known fractionation and separation techniques, such as vacuum distillation and solvent extraction.

The product mixture resulting from our process usually contain at least 6 weight percent o-cresol. More usually, the product mixture contains at least 10 weight percent o-cresol. Moreover, usually the product mixture will contain only slightly more prehnitenol (2,3,4,5-tetramethylphenol) than present in the feedstock. In any event, the amount of prehnitenol in the product mixture will usually be less than 8 weight percent.

ADVANTAGES OF OUR INVENTION

Use of the preferred catalysts provides several advantages over other processes, particularly processes which use silica-alumina, or alumina as the catalyst. First, the process results in a product containing more o-cresols. Secondly, the carbon and magnesium oxide do not have to be removed from the residue. This is due to the fact that they can be burned with the residue. By residue is meant the material remaining after the higher boiling methylated phenols are recovered from the reaction mass.

In order to illustrate the nature of the present invention still more clearly the following examples will be given. It is to be understood, however, that the invention is not to be limited to the specific conditions or details set forth in these examples except insofar as such limitations are specified in the appended claims.

EXAMPLE 1

The following were added to a 300 ml. autoclave:

| | |
|---|---|
| Phenol | 50 grams |
| Bottoms product (1) | 50 grams |
| Activated carbon (2) | 1 gram |

(1) A highly methylated phenol mixture containing large amounts of tetramethylphenols and pentamethylphenol
(2) From Pittsburgh Activated Carbon, "RB" pulverized The autoclave was evacuated. The temperature was increased to 420°–428° C. and a maximum pressure of 700 psig was observed at these conditions.

Samples of reaction products were taken at 0.5, 2 and 3 hours (termination of reaction).

The composition of the initial charge and of these samples is shown in the following table. The analysis was made by GLC (gas liquid chromatography).

| Time (Hrs) ° C Component (w/o) | Initial Charge | 0.5 420 | 2 428 | 3 40 (a) |
|---|---|---|---|---|
| Phenol | 38.0 | 33.2 | 25.5 | 26.1 |
| o-cresol | 4.2 | 8.7 | 12.9 | 14.4 |
| m,p-cresol | 0.2 | 0.4 | 0.6 | 0.8 |
| 2,6-xylenol | 0.2 | 0.7 | 2.4 | 2.8 |
| 2,4/2,5-xylenol | 0.4 | 0.9 | 1.6 | 1.8 |
| 2,3/3,5-xylenol | 0.4 | 1.1 | 2.7 | 3.5 |
| 3,4-xylenol | 0.1 | 0.3 | 1.0 | 1.1 |
| 2,4,6-TMP (1) | 0.2 | 0.3 | 0.4 | 0.4 |
| 2,3,6-TMP (1) | 1.3 | 1.4 | 1.0 | 0.7 |
| 2,4,5/2,3,5-TMP (1) | 3.8 | 5.8 | 7.8 | 7.1 |
| Pentamethylbenzene | 1.3 | 1.6 | 1.6 | 1.3 |
| 3,4,5/2,3,4-TMP (1) | 1.0 | 1.9 | 4.1 | 4.2 |
| 2,3,4,6/2,3,5,6-TeMP (2) | 12.0 | 9.3 | 4.4 | 2.5 |
| 2,3,4,5-TeMP (2) | 6.3 | 7.5 | 6.1 | 3.9 |
| Hexamethylbenzene | 0.4 | 0.4 | 0.3 | 0.2 |
| Pentamethylphenol | 9.2 | 5.0 | 1.2 | 0.4 |
| Higher b.p. | 21.0 | 21.6 | 26.4 | 28.8 |

(1) trimethylphenol
(2) tetramethylphenol
(a) after reduction of pressure and temperature

EXAMPLE 2

The following were added to a 300 ml. autoclave:

| | |
|---|---|
| Phenol | 50 grams |
| Bottoms product (1) | 50 grams |
| Magnesium oxide (2) | 1 gram |

(1) Same as in Example 1
(2) "Maglite D" from Merek & Co.

The autoclave was evacuated. The temperature was increased to 420°–424° C. and a maximum pressure of 62 atmospheres was observed at these conditions.

Samples of reaction product were taken at 1.2, 2.2 and 3.0 hours (termination of reaction).

The composition of the initial charge and of these samples is shown in the following table. The analysis was made by GLC (gas liquid chromatography).

| Time (Hrs) ° C Component (w/o) | Initial Charge | 1.2 424 | 2.2 420 | 3.0 40 (a) |
|---|---|---|---|---|
| Phenol | 41.4 | 30.7 | 25.5 | 26.4 |
| o-cresol | 2.3 | 11.7 | 14.1 | 15.2 |
| m,p-cresol | 0.4 | 0.3 | 0.5 | 0.6 |
| 2,6-xylenol | 0.1 | 1.7 | 2.8 | 2.8 |
| 2,4/2,5-xylenol | 0.3 | 1.3 | 1.7 | 1.6 |
| 2,3/3,5-xylenol | 0.4 | 2.1 | 3.2 | 3.6 |
| 3,4-xylenol | 0.1 | 0.9 | 1.3 | 1.4 |
| 2,4,6-TMP (1) | 0.1 | 0.4 | 0.4 | 0.3 |
| 2,3,6-TMP (1) | 1.3 | 1.2 | 0.8 | 0.6 |
| 2,4,5/2,3,5-TMP (1) | 3.1 | 7.5 | 7.7 | 7.1 |
| Pentamethylbenzene | 1.3 | 1.7 | 1.5 | 1.3 |
| 3,4,5/2,3,4-TMP (1) | 0.8 | 3.7 | 5.2 | 5.3 |
| 2,3,4,6/2,3,5,6-TeMP (2) | 12.9 | 6.6 | 3.5 | 2.4 |
| 2,3,4,5-TeMP (2) | 5.5 | 8.8 | 6.4 | 4.6 |
| Hexamethylbenzene | 0.5 | 0.4 | 0.4 | 0.3 |
| Pentamethylphenol | 11.6 | 3.1 | 1.0 | 0.6 |
| Higher b.p. | 18.0 | 18.0 | 24.0 | 25.9 |

(1) trimethylphenol
(2) tetramethylphenol
(a) after reduction of pressure and temperature

EXAMPLE 3

The following were added to a 300 ml. autoclave:

| | |
|---|---|
| Phenol | 110 grams |
| Bottoms product (1) | 90 grams |
| Activated carbon (2) | 2.5 grams |

(1) Same as in Example 1 and 2
(2) Same as in Example 1

The autoclave was evacuated. The temperature was increased to 420° C and a maximum pressure of 48 atmospheres. After 3 hours the reaction was terminated. The reaction product was distilled with the results of the distillation being:

| | | |
|---|---|---|
| Overhead | 174.60 g | 86.2% |
| Residue | 23.15 g | 11.4% |
| Loss (gas + H$_2$0) | 4.75 g | 2.4% |

The overhead product had the following composition as determined by GLC analysis.

| Overhead Analysis (w/o) | |
| --- | --- |
| Phenol | 46.4 |
| o-cresol | 13.5 |
| m,p-cresol | 0.5 |
| 2,6-xylenol | 1.4 |
| 2,4/2,5-xylenol | 1.1 |
| 3,5-xylenol | 1.2 |
| 2,3-xylenol | 0.5 |
| 3,4-xylenol | 0.7 |
| 2,4,6-TMP (1) | 0.3 |
| 2,3,6-TMP (1) | 1.1 |
| 2,4,5/2,3,5-TMP (1) | 7.7 |
| Pentamethylbenzene | 1.6 |
| 3,4,5/2,3,4-TMP (1) | 3.5 |
| 2,3,4,6/2,3,5,6-TeMP (2) | 6.3 |
| 2,3,4,5-TeMP (2) | 7.4 |
| Hexamethylbenzene | 0.4 |
| Pentamethylphenol | 2.3 |
| Xanthenes | 4.1 |

(1) trimethylphenol
(2) tetramethylphenol

Thus, having described the invention in detail, it will be understood by those skilled in the art that certain variations and modifications may be made without departing from the spirit and scope of the invention as defined herein and in the appended claims.

We claim:

1. A process for preparing cresols and xylenols which comprises reacting a mixture of tetramethylphenols and pentamethylphenol with phenol in the liquid phase in the presence of an effective amount of a catalyst selected from the group consisting of activated carbon, magnesium oxide, magnesium carbonate and magnesium hydroxide, said process being characterized further in that it is conducted at a temperature in the range of about 375° to about 500° C. and a pressure in the range of about 30 to about 125 atmospheres.

2. The process of claim 1 wherein the amount of catalyst is in the range of about 0.1 to about 5 weight percent based on the total amount of phenol, tetramethylphenols and pentamethylphenol.

3. The process of claim 2 wherein at least a stoichiometric amount, based on the tetramethylphenols and pentamethylphenol, of phenol is used.

4. The process of claim 3 wherein the catalyst is activated carbon.

5. The process of claim 3 wherein the catalyst is magnesium oxide.

6. A process for preparing cresols and xylenols which comprises reacting a mixture of tetramethylphenols and pentamethylphenol, said tetramethylphenols and pentamethylphenol being present in a complex mixture of methyl-substituted phenols which contain at least 10 weight percent tetramethylphenols and at least 10 weight percent pentamethylphenol, with phenol in the liquid phase in the presence of an effective amount of a catalyst selected from the group consisting of activated carbon and magnesium oxide said process being characterized further in that it is conducted at a temperature in the range of about 375° to about 500° C. and a pressure in the range of about 30 to about 125 atmospheres.

7. The process of claim 6 wherein at least a stoichiometric amount, based on the tetramethylphenols and pentamethylphenol, of phenol is used.

8. The process of claim 7 wherein the complex mixture of methyl-substituted phenols contains no more than 10 weight percent dimethylphenols.

9. The process of claim 8 wherein the catalyst is activated carbon.

10. The process of claim 8 wherein the catalyst is magnesium oxide.

* * * * *